United States Patent
Kazi

(10) Patent No.: US 11,328,187 B2
(45) Date of Patent: May 10, 2022

(54) INFORMATION PROCESSING APPARATUS AND INFORMATION PROCESSING METHOD

(71) Applicant: SONY SEMICONDUCTOR SOLUTIONS CORPORATION, Kanagawa (JP)

(72) Inventor: Mamun Kazi, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 154 days.

(21) Appl. No.: 16/640,523

(22) PCT Filed: Jun. 22, 2018

(86) PCT No.: PCT/JP2018/023726
§ 371 (c)(1),
(2) Date: Feb. 20, 2020

(87) PCT Pub. No.: WO2019/044135
PCT Pub. Date: Mar. 7, 2019

(65) Prior Publication Data
US 2020/0250498 A1 Aug. 6, 2020

(30) Foreign Application Priority Data
Aug. 31, 2017 (JP) .............................. JP2017-166484

(51) Int. Cl.
*G06K 9/00* (2022.01)
*G06K 9/62* (2022.01)
(Continued)

(52) U.S. Cl.
CPC ........... *G06K 9/6289* (2013.01); *G06V 10/40* (2022.01); *G06V 40/174* (2022.01)

(58) Field of Classification Search
CPC ..... G06K 9/6289; G06K 9/00302; G06K 9/46
See application file for complete search history.

(56) References Cited

U.S. PATENT DOCUMENTS

2008/0253695 A1* 10/2008 Sano ....................... A61B 5/165
382/305
2013/0217441 A1* 8/2013 Kitatani .................. G06F 1/163
455/556.1
(Continued)

FOREIGN PATENT DOCUMENTS

CN 103189817 A 7/2013
EP 2637078 A1 9/2013
(Continued)

OTHER PUBLICATIONS

Gaze Guided Object Recognition Using a Head-Mounted Eye Tracker, Takumi Toyama et al., DHFI, 2012, pp. 91-98 (Year: 2012).*

(Continued)

*Primary Examiner* — Jayesh A Patel
(74) *Attorney, Agent, or Firm* — Chip Law Group

(57) ABSTRACT

Provided is an information processing apparatus and an information processing method capable of reflecting a feeling of an image capturing person for each subject of a captured image in the captured image and reproducing the realistic feeling at the time of capturing. An information processing apparatus including a recognition unit that recognizes one or more subjects from a captured image, an estimation unit that estimates a feeling of an image capturing person for each of the recognized subjects on the basis of data regarding a line-of-sight of the image capturing person and sensor data of the image capturing person associated with the captured image, and an image processing unit that
(Continued)

performs image processing of reflecting the feeling for each of the subjects in the captured image.

17 Claims, 9 Drawing Sheets

(51) Int. Cl.
   *G06V 10/40*   (2022.01)
   *G06V 40/16*   (2022.01)

(56) References Cited

U.S. PATENT DOCUMENTS

| | | | |
|---|---|---|---|
| 2013/0243270 A1* | 9/2013 | Kamhi | H04N 21/458 |
| | | | 382/118 |
| 2014/0112540 A1* | 4/2014 | el Kaliouby | A61B 5/165 |
| | | | 382/103 |
| 2014/0289323 A1* | 9/2014 | Kutaragi | H04L 67/42 |
| | | | 709/203 |
| 2015/0063665 A1* | 3/2015 | Sasakido | G06K 9/00671 |
| | | | 382/128 |
| 2016/0096023 A1* | 4/2016 | Pan | H02J 7/025 |
| | | | 607/46 |
| 2017/0102765 A1* | 4/2017 | Yoneda | G06F 3/0304 |
| 2018/0268867 A1* | 9/2018 | Matsumoto | G11B 27/3081 |

FOREIGN PATENT DOCUMENTS

| | | | |
|---|---|---|---|
| JP | 2003-299013 A | 10/2003 | |
| JP | 4441172 B2 | 3/2010 | |
| JP | 2010-226623 A | 10/2010 | |
| JP | 2011-193275 A | 9/2011 | |
| JP | 2012-257112 A | 12/2012 | |
| JP | 2015-046069 A | 3/2015 | |
| JP | 2015046069 A * | 3/2015 | ......... G06K 9/00362 |
| WO | 2012/060039 A1 | 5/2012 | |

OTHER PUBLICATIONS

Photo and Video Quality Evaluation: Focusing on the Subject, Yiwen Luo et al., Springer, 2008, pp. 386-399 (Year: 2008).*

Improving Saliency Detection Based on Modeling Photographer's Intention, Xiaoying Ding et al., IEEE, 2019, pp. 124-134 (Year: 2019).*

International Search Report and Written Opinion of PCT Application No. PCT/JP2018/023726, dated Aug. 21, 2018, 10 pages of ISRWO.

* cited by examiner

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2018/023726 filed on Jun. 22, 2018, which claims priority benefit of Japanese Patent Application No. JP 2017-166484 filed in the Japan Patent Office on Aug. 31, 2017. Each of the above-referenced applications is hereby incorporated herein by reference in its entirety.

TECHNICAL FIELD

The present disclosure relates to an information processing apparatus, an information processing method, and a program.

BACKGROUND ART

Recently, digital cameras have been widely used. Various techniques for browsing, management, treatment, and the like of an acquired captured image are proposed.

In relation to technology related to a captured image, for example, Patent Document 1 below discloses technology in which emotional information (specifically, "favorite" "important", and "field of feeling such as fear, anger, and happiness") of a user to a digital image and a user identifier are stored, the digital image is classified, and retrieval of the digital image based on the emotional information can be performed.

Furthermore, Patent Document 2 below discloses image processing of brightening or darkening an entire captured image on the basis of analysis of feelings of an image capturing person (specifically, delightful expression or sad expression).

Furthermore, Patent Document 3 below discloses an apparatus that acquires and records an image, voice, human body information (eyeball motion, the number of heart beats, and the number of blinks), and environmental information (e.g., acceleration, temperature, humidity, and weather) as experience information around an experienced person, and that reproduces the realistic feeling at the time of capturing.

CITATION LIST

Patent Document

Patent Document 1: Japanese Patent No. 4441172
Patent Document 2: Japanese Patent Application Laid-Open No. 2012-257112
Patent Document 3: Japanese Patent Application Laid-Open No. 2003-299013

SUMMARY OF THE INVENTION

Problems to be Solved by the Invention

Here, although, in all of the above-described traditional techniques, an image capturing person is assumed to have a single feeling for the entire captured image, the image capturing person does not necessarily have a single interesting target and feeling for the entire captured image. It is conceivable that the image capturing person has an interesting target and a feeling for a specific subject or each subject appearing in the captured image.

Then, in the disclosure, there is proposed an information processing apparatus, an information processing method, and a program capable of reflecting a feeling of an image capturing person for each subject of a captured image in the captured image and reproducing the realistic feeling at the time of capturing.

Solutions to Problems

According to the disclosure, there is proposed an information processing apparatus including: a recognition unit that recognizes one or more subjects from a captured image; an estimation unit that estimates a feeling of an image capturing person for each of the recognized subjects on the basis of data regarding a line-of-sight of the image capturing person and sensor data of the image capturing person associated with the captured image; and an image processing unit that performs image processing of reflecting the feeling for each of the subjects in the captured image.

According to the disclosure, there is proposed an information processing method including: recognizing, by a processor, one or more subjects from a captured image; estimating, by the processor, a feeling of an image capturing person for each of the recognized subjects on the basis of data regarding a line-of-sight of the image capturing person and sensor data of the image capturing person associated with the captured image; and performing, by the processor, image processing of reflecting the feeling for each of the subjects in the captured image.

According to the disclosure, there is proposed a program causing a computer to function as: a recognition unit that recognizes one or more subjects from a captured image; an estimation unit that estimates a feeling of an image capturing person for each of the recognized subjects on the basis of data regarding a line-of-sight of the image capturing person and sensor data of the image capturing person associated with the captured image; and an image processing unit that performs image processing of reflecting the feeling for each of the subjects in the captured image.

Effects of the Invention

As described above, according to the disclosure, a feeling of an image capturing person for each subject of a captured image can be reflected in the captured image, and the realistic feeling at the time of capturing can be reproduced.

Note that the above-described effect is not necessarily limited, and, along with or in place of the above-described effect, any of the effects illustrated in the present specification, or other effects that can be grasped from the present specification may be exhibited.

MODE FOR CARRYING OUT THE INVENTION

A preferred embodiment of the disclosure will be described in detail below with reference to the accompanying drawings. Note that, in the present specification and the drawings, the same signs are attached to components having substantially the same functional configuration, and redundant description will be omitted.

Figure 1:
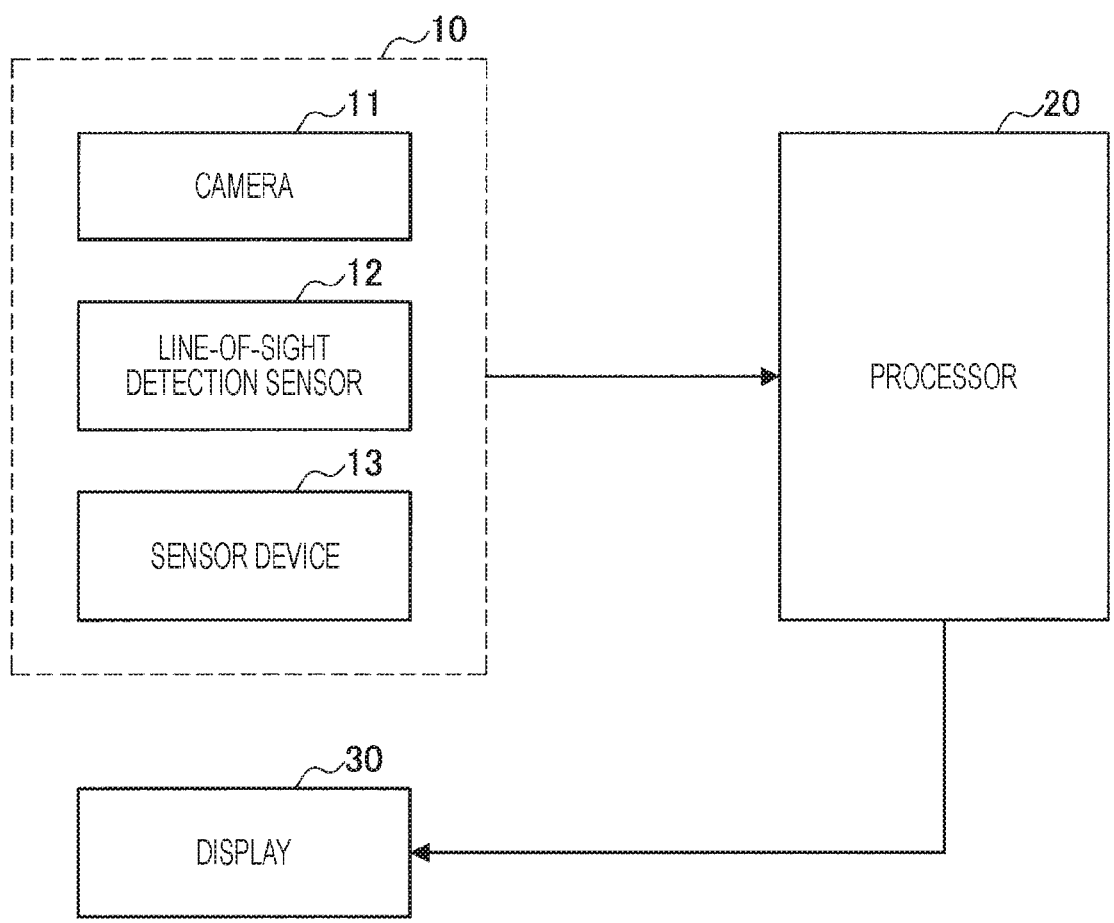
FIG. 1 outlines an information processing system according to one embodiment of the disclosure.

Furthermore, the description will be given in the following order.
1. Outline of Information Processing System According to One Embodiment of Disclosure
2. Configuration of Processor 20
3. Operation Processing
4. Example of Image Treatment
5. Hardware Configuration
6. Conclusion 1. Outline of Information Processing System According to One Embodiment of Disclosure FIG. 1 outlines an information processing system according to one embodiment of the disclosure. As illustrated in FIG. 1, an information processing system 1 according to the embodiment includes an input apparatus 10, a processor 20, and a display 30 (one example of an output apparatus).

The input apparatus 10 includes a camera 11, a line-of-sight detection sensor 12, and one or more sensor devices 13. The camera 11 acquires image data. The line-of-sight detection sensor 12 detects a line-of-sight of an image capturing person. The sensor devices 13 sense a state of the image capturing person, and acquire various pieces of sensor data. The input apparatus 10 may include a single apparatus or a plurality of apparatuses. Note that, in a case where the input apparatus 10 includes a plurality of apparatuses, a special sensor for data synchronization may be mounted in each input device.

The camera 11 may be a camera mounted in various terminal apparatuses such as a smartphone, a mobile phone terminal, glasses, and a head mounted display (HMD) in addition to a camera apparatus such as a digital camera and a video camera. The camera 11 includes, for example, a lens system, a drive system, and a solid-state imaging element array. The lens system includes, for example, an imaging lens, a diaphragm, a zoom lens, and a focus lens. The drive system causes the lens system to perform focusing operation and zooming operation. The solid-state imaging element array performs photoelectric conversion on imaging light obtained at the lens system to generate an imaging signal. The solid-state imaging element array may be implemented by, for example, a charge coupled device (CCD) sensor array and a complementary metal oxide semiconductor (CMOS) sensor array.

The line-of-sight detection sensor 12 is a sensor device that detects a line-of-sight of an image capturing person, and is mounted in, for example, the camera 11. The line-of-sight detection sensor 12 can preferably detect a line-of-sight with the position of a body (face) being fixed to the camera 11 (e.g., a viewfinder with an infrared line-of-sight tracker attached to the camera 11, an inward-facing camera for detecting a line-of-sight mounted on glasses with a capturing camera, and the like). Furthermore, the line-of-sight detection sensor 12 can also be achieved by a front camera (inward-facing camera) of a smartphone. For example, a front camera of a smartphone can detect (estimate) a line-of-sight by detecting the outline of the face of an image capturing person, identifying the position of an eye (or identifying the position of glasses worn by the image capturing person, or performing identification by detecting a marker of the glasses), and detecting, for example, the direction of the face and the motion of the eye (position and state of the pupil and the iris).

The sensor device 13 is assumed to be, for example, a biosensor (e.g., arterial sensor, vein sensor, pulse sensor, heart rate sensor, body temperature sensor, sweat sensor, blood pressure sensor, respiration sensor, myoelectric sensor, and brain wave sensor), a microphone (voice sensor), a camera sensor, a smile sensor (smile detection), or a motion sensor (acceleration sensor, gyro sensor, and geomagnetic sensor). The smile sensor can detect a smile index by performing face analysis from a captured image obtained by imaging the face of an image capturing person. Specifically, for example, the smile sensor calculates a smile index (degree of a smile) of the image capturing person by, for example, analysis of the shape of a mouth and the state of an eye and machine learning. The sensor device 13 may be integrated with the camera 11 or the line-of-sight detection sensor 12, or may be a single device (e.g., wearable device worn by a user). Furthermore, the sensor device 13 may be disposed around the user (in a capturing environment). For example, monitoring cameras, microphones, biosensors, and the like installed in towns are assumed.

BACKGROUND

Here, there is a problem that it is difficult to express the realistic feeling of a landscape that is visible to naked eyes at the time of capturing a picture in a captured image. At the time of capturing a picture, there occurs a phenomenon in which a specific subject looks larger by a person seeing the subject while paying attention and directing some feeling to the subject. The phenomenon, however, occurs in the brain of the person, and is not reflected in the picture. As a result, in a case where the person see the captured picture, the person may feel that the captured image is different from the scenery that has been recognized at the time of capturing.

Specifically, although humans have a field of view covering approximately 180 to 210 degrees on the right and left, the retina has high sensitivity at a central part (line-of-sight direction, that is, gaze part), and the central part (also referred to as "central vision") covers only approximately two degrees. There is a theory that, in a case where a person gazes at a specific subject at the time of capturing, the field of view of the person covers a range equivalent to that covered by a super-telephoto lens, and the person unconsciously zooms the subject (or trims the surroundings) in his/her brain, so that the person feels a greater presence of the subject. In contrast, there also occurs a phenomenon in which the person feels a smaller presence for a subject that has entered the view but is not gazed at or for an object that the person does not want to see (person sometimes does not notice the presence of the subject).

Figure 2:
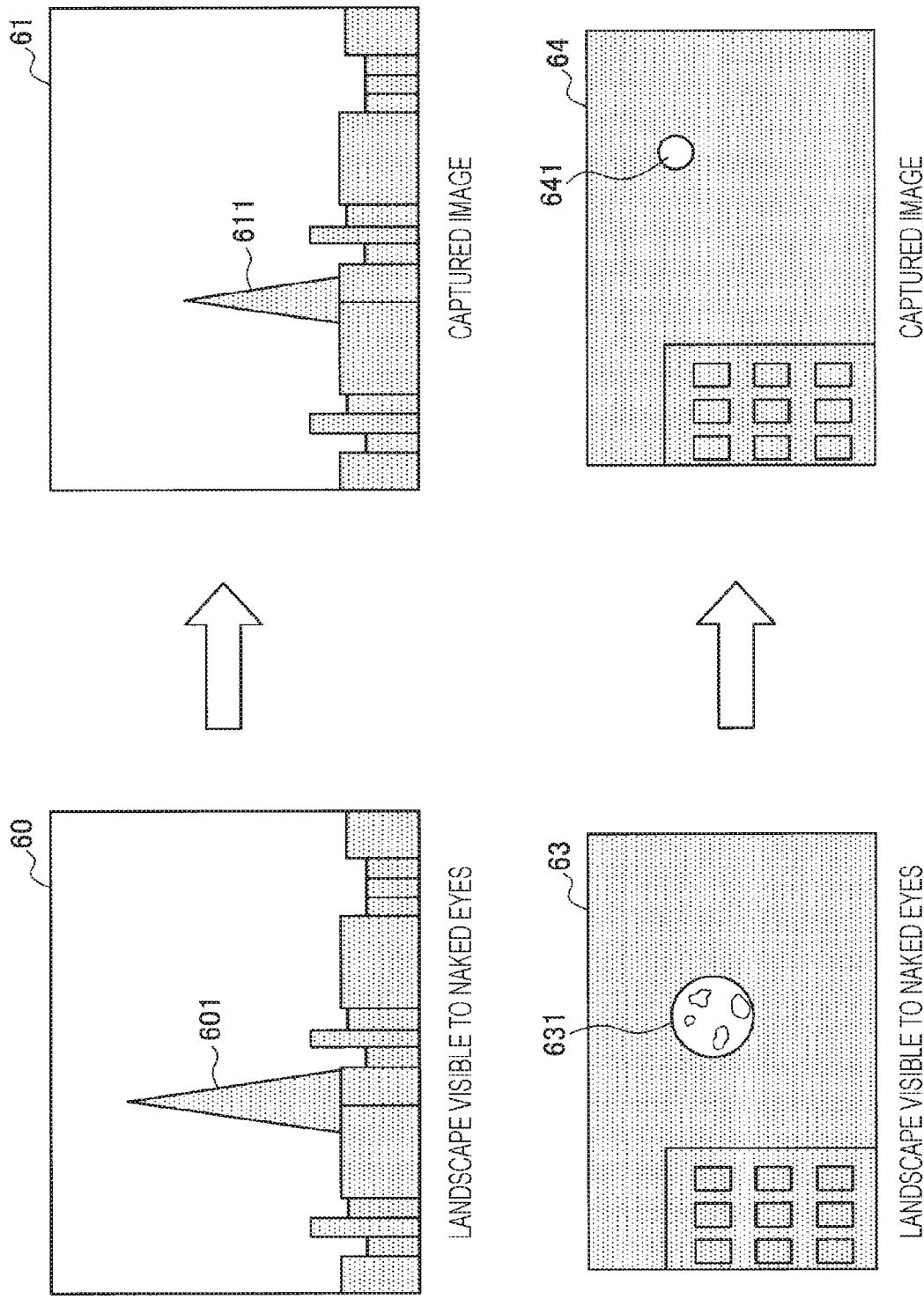
FIG. 2 illustrates the difference in impression between how a landscape looks to naked eyes at the time of capturing and how the landscape looks in an actual captured image.

FIG. 2 illustrates the difference in impression between how a landscape looks to naked eyes at the time of capturing and how the landscape looks in an actual captured image. For example, as illustrated in the upper part of FIG. 2, in a case where an image capturing person pays attention to a landmark 601 among a plurality of subjects in an angle of view in a landscape 60 of a townscape viewed by naked eyes and has a positive feeling that the landmark 601 gives wonderful scenery, the image capturing person unconsciously feels a greater presence of the landmark 601 (than that of another subject) in his/her brain. Such feeling of the image capturing person is not reflected in a captured image 61 of the landscape 60 captured at this time, and a landmark 611 is smaller than that in impression as seen by the naked eyes.

Furthermore, as illustrated in the lower part of FIG. 2, a similar phenomenon occurs in a case of capturing a picture of the moon. In a case where an image capturing person pays attention to a moon 631 among a plurality of subjects in an angle of view in a landscape 63 of the moon viewed by naked eyes and has a positive feeling that the moon 631 gives wonderful scenery, the image capturing person unconsciously feels a greater presence of the moon 631 (than that of another subject) in his/her brain. Such feeling of the image capturing person is not reflected in a captured image 64 of the landscape 63 captured at this time, and a moon 641 is smaller than that in impression as seen by the naked eyes.

In this way, the presence of a subject in an angle of view is increased or decreased depending on the degree of attention and feeling of an image capturing person. Since such degree of attention and feeling of the image capturing person to the subject, however, are lost at the time of replaying a picture or a moving image, the image capturing person has impression different from that at the time of capturing.

Then, in the embodiment, data regarding a degree of attention and feeling of an image capturing person is recorded for each subject appearing in image data together with data of a captured image (which is imaging data of a still image or moving image, and also hereinafter referred to as a "captured image"). Predetermined image processing is performed on the basis of the recorded data. An image can thereby be replayed while bringing the image closer to how a subject looks to (naked eyes of) an image capturing person (impression), and the realistic feeling can be reproduced. Note that the data regarding the degree of attention and feeling of an image capturing person is one example of data regarding factors that influence the presence of a subject felt by the image capturing person.

This can reduce the difference between a landscape that the image capturing person has seen with naked eyes and a captured image, and improve an experience of a person who sees the image (video). Furthermore, if a special scene that an image capturing person can experience only at that time can be captured by reflecting a feeling of the person to an image, new ways of enjoying pictures and moving images are provided.

Specifically, in the information processing system 1 illustrated in FIG. 1, the input apparatus 10 outputs a captured image, data regarding a line-of-sight of the image capturing person, and sensor data of the image capturing person to the processor 20. The captured image is acquired by the camera 11. The data regarding a line-of-sight of the image capturing person (time-series data regarding a line-of-sight associated with time for synchronization) is detected by the line-of-sight detection sensor 12. The sensor data is acquired by the sensor device 13.

The processor 20 calculates the degree of attention for each subject on the basis of the data regarding a line-of-sight of the image capturing person, analyzes the sensor data of the image capturing person, and estimates a feeling of the image capturing person for each subject (feeling of the image capturing person directed to each subject). Then, the processor 20 treats the captured image on the basis of the degree of attention for each subject and information regarding estimated feeling (feeling index). The processor 20 generates an image closer to the landscape that the image capturing person has seen (felt) with naked eyes. The processor 20 outputs the generated image to the display 30.

The processor 20 may treat the captured image at the time of capturing in real time, and display the treated image on the display 30 to enable the image capturing person to check the image. The processor 20 may treat the captured image at the time of receiving a request from the display 30. The processor 20 may appropriately treat the captured image at any timing on the side of the processor 20 without depending on either timing. The processor 20 may be, for example, a server disposed on the cloud side.

Furthermore, the information processing system 1 illustrated in FIG. 1 is one example of system configurations, and the disclosure is not limited thereto. For example, all configurations of the information processing system 1 illustrated in FIG. 1 may be implemented by a single apparatus or a plurality of apparatuses in any combination. For example, at least one of the camera 11, the line-of-sight detection sensor 12, or the sensor device 13 of the input apparatus 10 and all or part of the processor 20 may be implemented by the same apparatus.

Here, one example of specific system configurations will be described with reference to FIGS. 3 and 4.

Figure 3:
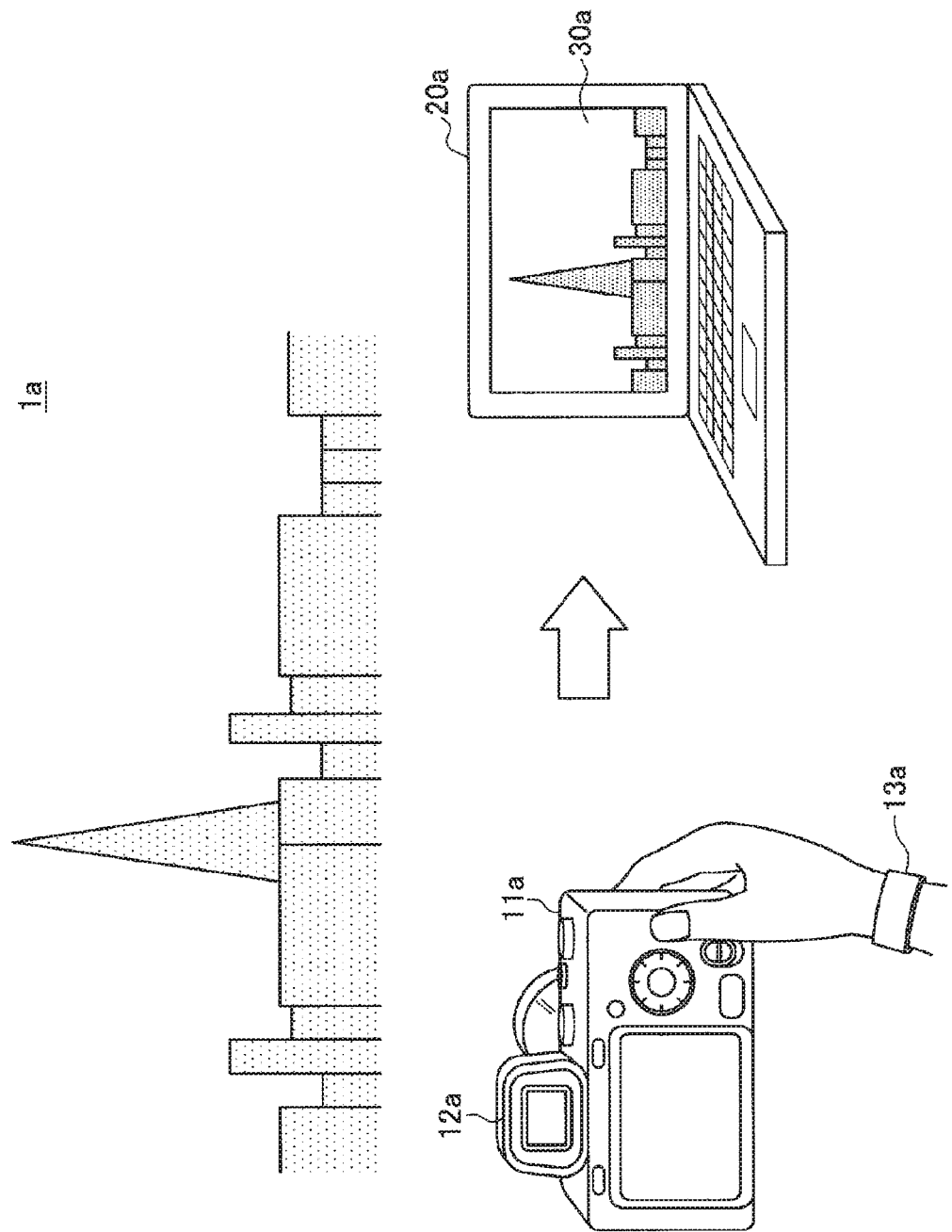
FIG. 3 illustrates one example of specific system configurations according to the embodiment.

FIG. 3 illustrates one example of specific system configurations according to the embodiment. As illustrated in FIG. 3, an information processing system 1a according to the embodiment may include a camera apparatus 11a, a wearable device (sensor device 13a), and an image processor 20a. The camera apparatus 11a is provided with a viewfinder (line-of-sight detection sensor 12a) capable of detecting, for example, a line-of-sight of an image capturing person. The wearable device (sensor device 13a) is worn on a body of a user. The image processor 20a includes the processor 20 and the display 30.

The viewfinder (line-of-sight detection sensor 12a) is mounted with, for example, an infrared line-of-sight tracker, and can detect a line-of-sight (pupil motion) by reflection of infrared rays applied to an eye of the image capturing person looking through the viewfinder. Furthermore, the viewfinder (line-of-sight detection sensor 12a) may be detachable from the camera apparatus 11a.

The wearable device (sensor device 13a) is, for example, a wristband worn on an arm of the user (image capturing person), and mounted with, for example, an arterial sensor in one example of the biosensor. The wearable device (sensor device 13a) transmits the detected arterial data in a wireless/wired manner by using the camera apparatus 11a.

The camera apparatus 11a associates and records a captured image, data (time-series) regarding a line-of-sight of the image capturing person, and biosensor data (time-series) such as data regarding an artery of the image capturing person. The data regarding a line-of-sight of the image capturing person has been acquired from the viewfinder (line-of-sight detection sensor 12a) at the time of capturing the captured image (e.g., from a predetermined period of time before imaging to the imaging, such as from when a shutter is half-pressed to fully pressed). The biosensor data is acquired from the wearable device (sensor device 13a) at the time of the same capturing.

The image processor 20a is an information processing apparatus in which the processor 20 and the display 30 are integrated. The image processor 20a is implemented by, for example, a personal computer (PC), a tablet terminal, a smartphone, a mobile phone terminal, a game machine, a television apparatus, a projector, and the like. The image processor 20a acquires data recorded by the above-described camera apparatus 11a in a wired/wireless manner or from a storage medium in which the recorded data is written. The image processor 20a calculates a degree of attention and feeling of the image capturing person for each of one or more subjects appearing in the captured image on the basis of the acquired data. Then, the captured image is treated on the basis of the calculation result. The captured image that reflects a feeling of the image capturing person and is closer to the state seen (felt) with naked eyes is displayed on a display unit 30a.

Figure 4:
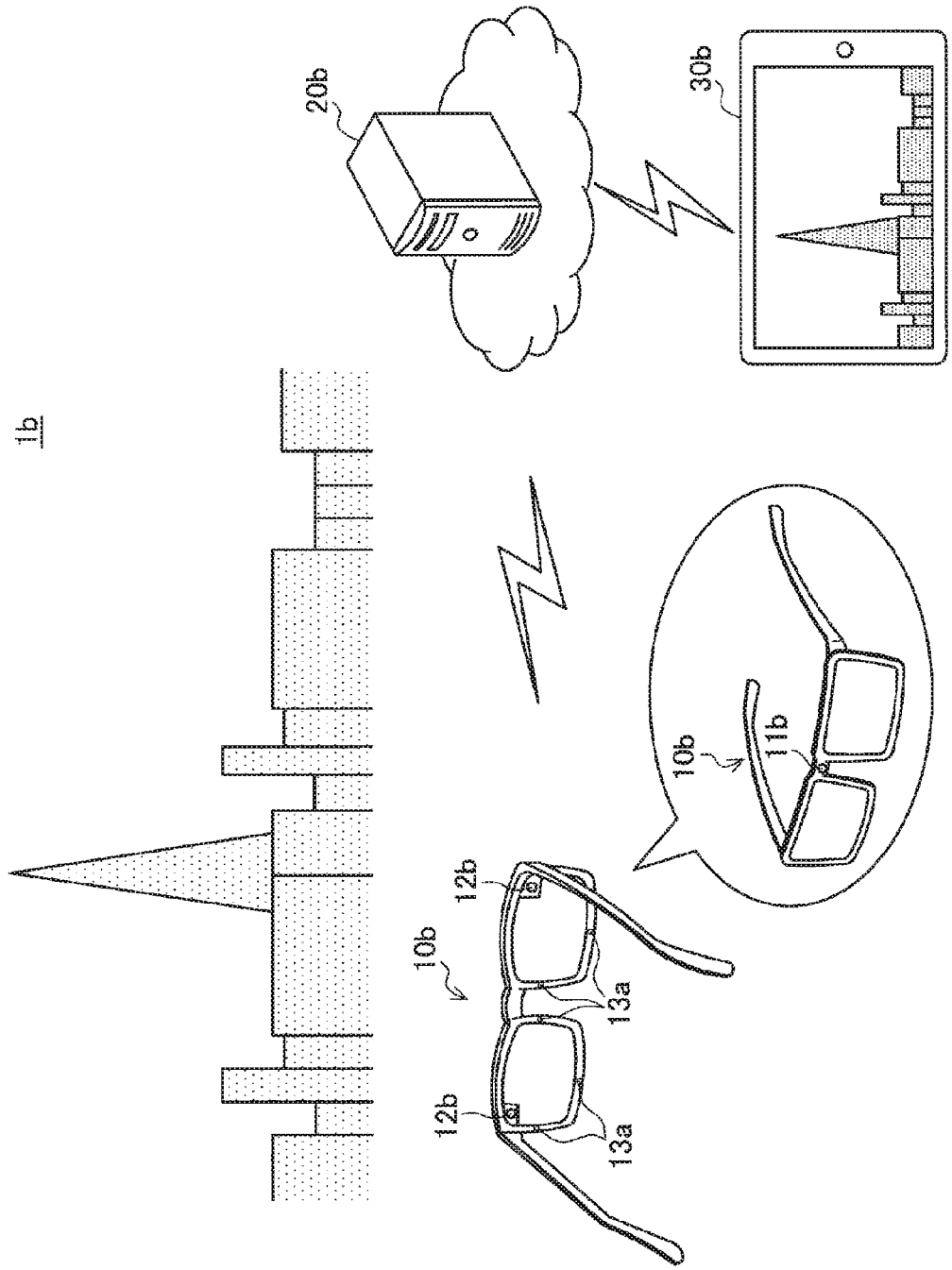
FIG. 4 illustrates another example of the specific system configurations according to the embodiment.

FIG. 4 illustrates another example of specific system configurations according to the embodiment. As illustrated in FIG. 4, an information processing system 1b according to the embodiment may include, for example, a glass apparatus 10b (one example of the input apparatus 10) worn by an image capturing person, a server 20b (one example of the processor 20), and an information processing terminal 30b (one example of the display 30).

The glass apparatus 10b includes an inward-facing camera 12b (one example of the line-of-sight detection sensor 12) for tracking a line-of-sight, a capturing camera 11b (one example of the camera 11), and a biosensor 13a (one example of the sensor device 13). The inward-facing camera 12b images an eye of a user wearing the glass apparatus 10b, and detects a line-of-sight. Furthermore, the capturing camera 11b images a line-of-sight direction (view) of the user wearing the glass apparatus 10b. A shutter trigger can be performed by, for example, predetermined operation of the user (e.g., hitting the glass apparatus 10b predetermined times/with predetermined rhythm, blinking predetermined times/with predetermined rhythm/slowly, whispering a predetermined keyword, shaking a head, nodding, and the like). These operations are detected by, for example, a touch sensor, an acceleration sensor, a gyro sensor, a microphone, and the inward-facing camera 12b provided in the glass apparatus 10b. Alternatively, the shutter trigger may be transmitted by user operations (e.g., screen operation, touch operation, and gesture) to various user terminals such as a smartphone, a smart band, and a smart earring paired with the glass apparatus 10b to the glass apparatus 10b.

Furthermore, the biosensor 13a detects, for example, an expression (skin deformations around an eye and between his/her brows and motion of muscles of expression) and sweating of the user. Specifically, the biosensor 13a is implemented by, for example, a skin capacitance-based sensor, a reflected-light sensor, and the like. One or a plurality of biosensors 13a is provided, for example, around a lens inside the glass apparatus 10b.

The glass apparatus 10b associates and records a captured image, data (time-series data) regarding a line-of-sight of the image capturing person, and biosensor data (time-series data) such as data regarding muscles of expression or data regarding sweating of the image capturing person. The captured image is captured by the capturing camera 11b. The data regarding a line-of-sight of the image capturing person has been acquired from the inward-facing camera 12b at the time of capturing the captured image (e.g., from a predetermined period of time before release of a shutter (transmitting a shutter trigger) to the release of the shutter). The biosensor data has been acquired from the biosensor 13a at the time of the same capturing. Furthermore, the glass apparatus 10b transmits the associated data (captured image, data regarding a line-of-sight, and biosensor data) to the server 20b via a network.

The server 20b calculates a degree of attention and feeling of the image capturing person for each of one or more subjects appearing in the captured image on the basis of the data that has been transmitted from the glass apparatus 10b, treats the captured image on the basis of the calculation result, and generates a captured image that reflects feeling of the image capturing person and is closer to the state seen (felt) with naked eyes.

The information processing terminal 30b is an information processing apparatus having the configuration of the display 30. The information processing terminal 30b is implemented by, for example, a personal computer (PC), a tablet terminal, a smartphone, a mobile phone terminal, a game machine, a television apparatus, a projector, and the like. The information processing terminal 30b receives the treated captured image from the server 20b via the network, and displays the image on the display unit.

The above-described specific example of the system configuration is one example, and the system configuration of the disclosure is not limited thereto. A system configuration in another combination is naturally falls within the scope of the disclosure.

For example, at least one of the camera 11, the line-of-sight detection sensor 12, or the sensor device 13 of the input apparatus 10 and the display 30 may be integrated, and communicably connected to the processor 20 via the network. That is, for example, the camera apparatus 11a and the display 30 illustrated in FIG. 3 may be configured by a single apparatus (camera apparatus), and communicably connected to the server 20b illustrated in FIG. 4. Furthermore, the functions of the processor 20 may be distributed to other apparatuses. For example, the camera apparatus 11a may recognize a subject, and calculate a degree of attention and feeling for each subject. The server 20b may perform image treatment processing based on the captured image and the calculated data.

Furthermore, the sensor device 13 is not limited to detection of sensor data, and may process and output the detected data. For example, the sensor device 13 may calculate a smile index from a captured image obtained by imaging the face of the image capturing person and muscles of expression, and output the calculated smile index (so-called smile sensor).

An information processing system according to one embodiment of the disclosure has been described above. Then, the specific configuration of the processor 20 included in the information processing system according to the embodiment will be described with reference to the drawings.

2. Configuration of Processor 20

Figure 5:
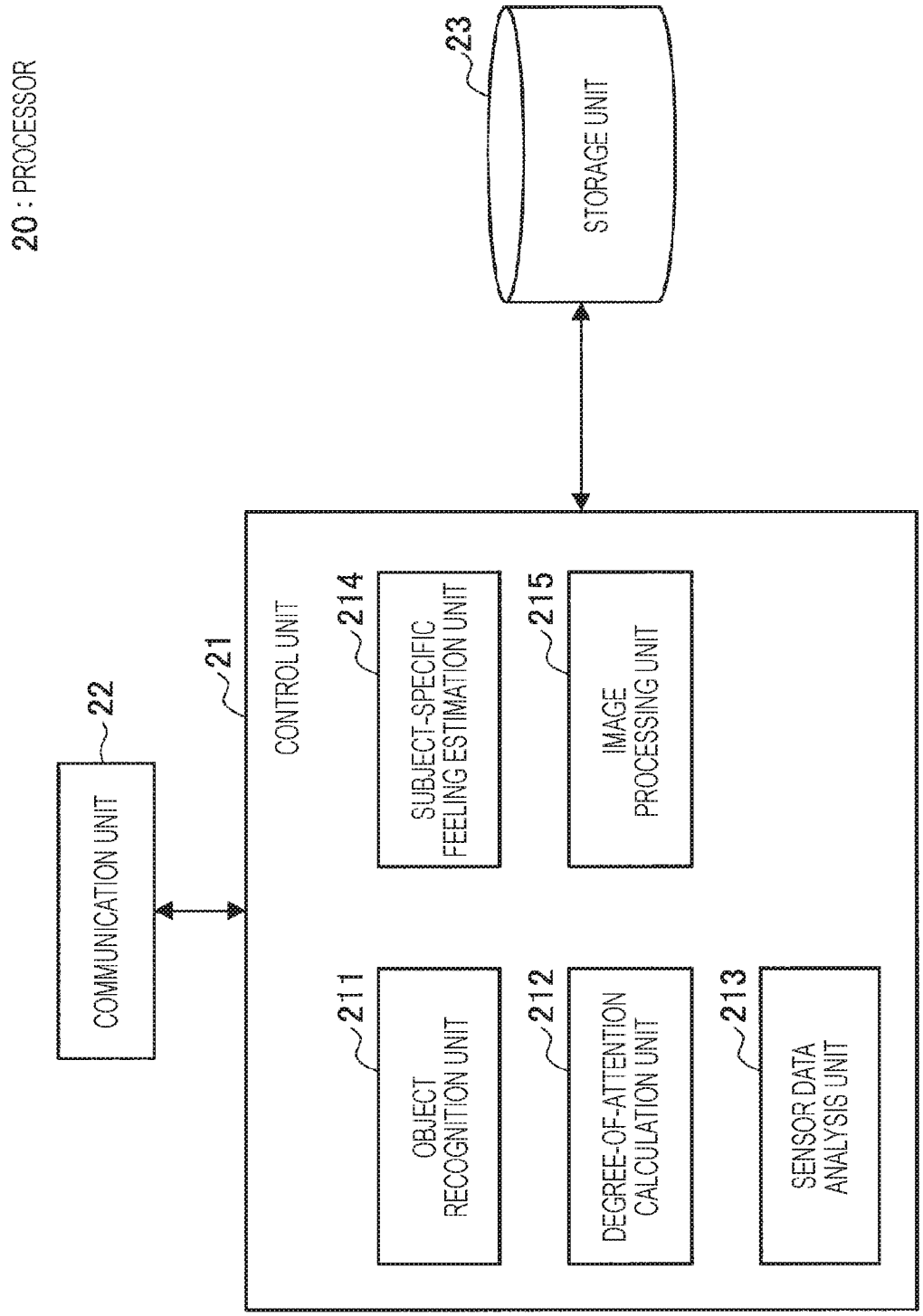
FIG. 5 is a block diagram illustrating one example of the configuration of a processor according to the embodiment.

FIG. 5 is a block diagram illustrating one example of the configuration of the processor 20 according to the embodiment. As illustrated in FIG. 5, the processor 20 includes a control unit 21, a communication unit 22, and a storage unit 23.

The control unit 21 functions as an arithmetic processor and a controller, and controls overall operation in the processor 20 in accordance with various programs. The control unit 21 is implemented by, for example, an electronic circuit such as a central processing unit (CPU) and a microprocessor. Furthermore, the control unit 21 may include a read only memory (ROM) and a random access memory (RAM). For example, a program and an arithmetic parameter to be used are stored in the ROM. The RAM temporarily stores, for example, a parameter that appropriately changes.

Furthermore, as illustrated in FIG. 5, the control unit 21 according to the embodiment also functions as an object recognition unit 211, a degree-of-attention calculation unit 212, a sensor data analysis unit 213, a subject-specific feeling estimation unit 214, and an image processing unit 215.

Figure 6:
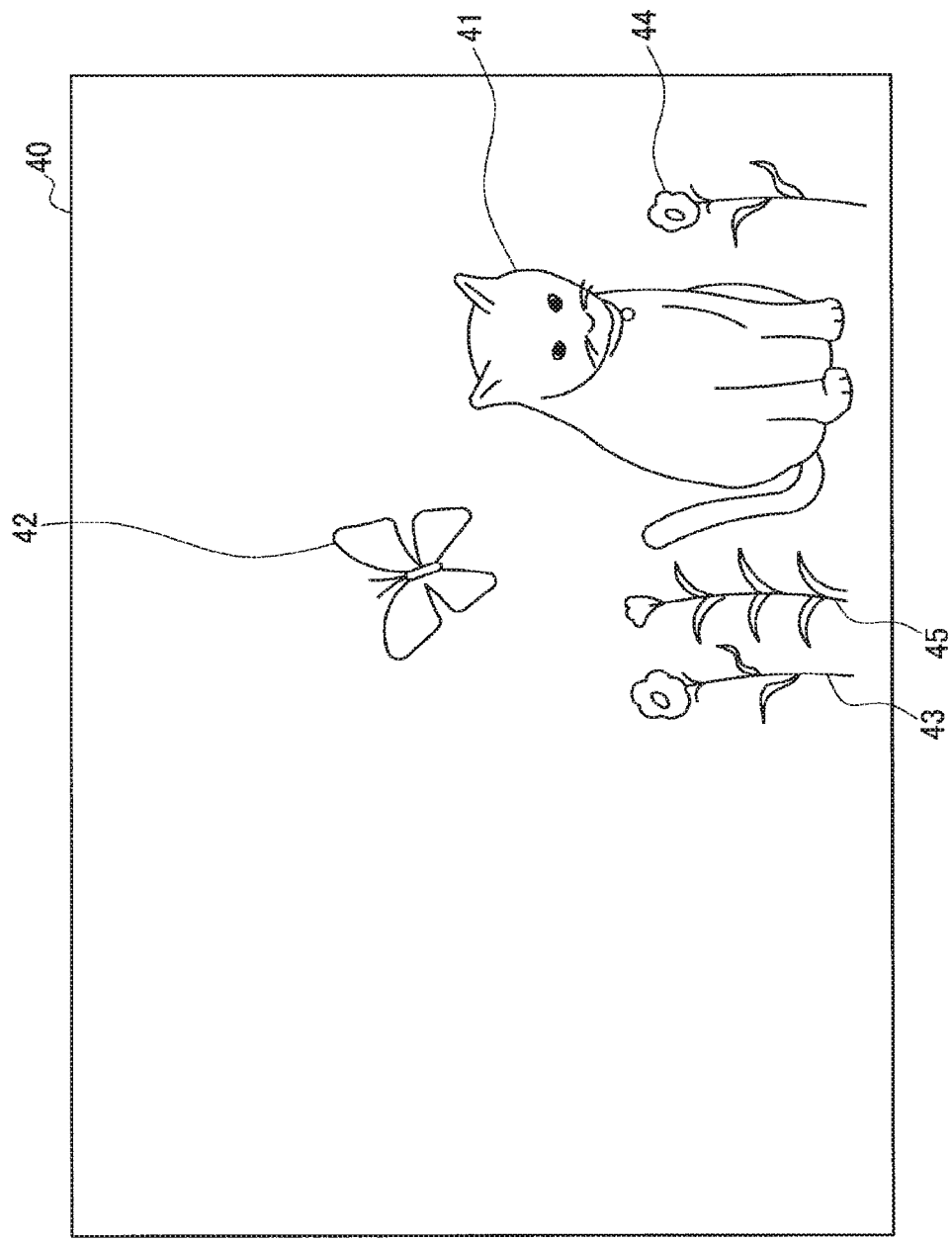
FIG. 6 illustrates detection of a subject of a captured image according to the embodiment.

The object recognition unit 211 recognizes (detects) an object (subject) by analyzing a captured image. Specifically, the object recognition unit 211 identifies the boundary (x, y coordinates) of the object, and gives an ID to each detected object. FIG. 6 illustrates detection of a subject. For example, the object recognition unit 211 recognizes a subject 41 (cat), a subject 42 (butterfly), a subject 43 (first flower), a subject (second flower), and a subject 45 (third flower) from a captured image 40 illustrated in FIG. 6. The object recognition unit 211 gives an ID (e.g., cat (x, y): ID1, butterfly (x, y): ID2, first flower (x, y): ID3, second flower (x, y): ID4, and third flower (x, y): ID5) to each subject. Note that algorithm for object recognition is not particularly limited. Technology such as, for example, generally used general object recognition and specific object recognition may be used. In the general object recognition, an object is recognized by extracting features from an input image and classifying the features by using a learned classifier. In the specific object recognition, determination is performed by extracting features from an input image and collating the features with a database generated in advance. Furthermore, it is sufficient if the presence of some kind of object can be extracted (boundary of the object can be identified) even without determining what the object is (e.g., category name).

The degree-of-attention calculation unit 212 calculates a degree of attention of the image capturing person for each subject on the basis of data regarding a line-of-sight of the image capturing person. The data regarding a line-of-sight is time-series data indicating when and where the image capturing person has looked. Sampling has been performed before imaging, such as from when a shutter is half-pressed to fully pressed, for example. The degree-of-attention calculation unit 212 calculates a period of time during which a line-of-sight has been fixed in a pixel of each object on the basis of a recognition result regarding an object (subject) in the captured image from the object recognition unit 211 and the data regarding a line-of-sight. Whether or not the line-of-sight has been fixed may be determined by whether or not, for example, stay period of time, motion, or the like of the line-of-sight (movement speed of the line-of-sight) in a pixel of the subject satisfies a predetermined condition. A longer period of time in which a line-of-sight is fixed means that the object has been paid attention to (higher degree of attention). For example, the period of time in which a line-of-sight is fixed for a plurality of objects (subjects) may be calculated as a degree of attention as follows.

Subject ID1: 100 msec
Subject ID2: 2000 msec
Subject ID3: 0 msec
Subject ID4: 0 msec
Subject ID5: 200 msec Note that which subject the image capturing person has paid attention to is not determined only by the method of detection from data regarding a line-of-sight of the image capturing person, and may be determined on the basis of a manual operation of the image capturing person. The image capturing person sometimes performs some kind of operation on a target to be paid attention to, such as tapping a subject attracting attention among a plurality of subjects appearing in a through image displayed on, for example, a camera apparatus or a smartphone at the time of capturing and focusing on the subject, and pinching out and enlarging the subject. Alternatively, the image capturing person may be prompted to perform an operation for explicitly specifying a subject attracting attention (desired to be captured). The degree-of-attention calculation unit 212 can acquire such information regarding an operation of the image capturing person together with the captured image, and calculate a degree of attention for each subject on the basis of the operation information. Furthermore, the degree-of-attention calculation unit 212 may calculate the degree of attention for each subject by using both the approach based on data regarding a line-of-sight and the approach based on user operation.

The sensor data analysis unit 213 analyzes various pieces of sensor data obtained by sensing the image capturing person at the time of capturing for each subject. Here, the sensor data is time-series data indicating when and how the state of the image capturing person has been. Sampling is performed before imaging, such as from when a shutter is half-pressed to fully pressed, for example. The sensor data is assumed to include, for example, biological data (e.g., artery, vein, pulse, heart rate, body temperature, sweating, blood pressure, respiration, myoelectric value, brain wave, and the like), voice (speech) data, imaging data, motion sensor data (e.g., acceleration, angular speed, geomagnetic sensor value, and the like), processing data (e.g., smile index calculated from, for example, a captured image or muscles of expression, data acquired by machine learning, and the like) calculated from one or more pieces of sensor data, and the like.

For example, the sensor data analysis unit 213 analyzes the number of fixation of a line-of-sight in a pixel of each object and sensor data for each time zone in which a line-of-sight has been fixed for each object on the basis of a recognition result regarding an object (subject) in the captured image from the object recognition unit 211, the data regarding a line-of-sight, and the sensor data. For example, an average value of pieces of biological data may be calculated or a smile index may be associated for each time zone in which a line-of-sight has been fixed to a subject. Specifically, for example, sensor data for each number of fixation of a line-of-sight of the image capturing person can be analyzed for a plurality of objects (subjects) as follows.

Subject ID1: Line-of-sight fixation first time . . . Pulse average of 78/sec and Smile index of 10
Subject ID2: Line-of-sight fixation first time . . . Pulse average of 90/sec and Smile index of 70
   Line-of-sight fixation second time . . . Pulse average of 90/sec and Smile index of 100
Subject ID3: NA
Subject ID4: NA
Subject ID5: Line-of-sight fixation first time . . . Pulse average of 60/sec and Smile index of 0

The subject-specific feeling estimation unit 214 estimates a feeling of the image capturing person for each subject on the basis of the degree of attention for each subject calculated by the degree-of-attention calculation unit 212 and an analysis result regarding sensor data for the subject calculated by the sensor data analysis unit 213. Here, "feeling" may be classified into six basic feelings and an application feeling. The six basic feelings include, for example, "joy", "anger", "grief", "fun", "love", and "hate". The application feeling is obtained by combining these two or more basic feelings. Alternatively, for example, a circumplex model of feelings that has been proposed by Russell may be used. In this model, feelings are circularly arranged in a plane represented by two-dimensional axes of "activated-deactivated" and "pleasant-unpleasant". In the circumplex model of Russell, synonyms such as happiness and joy are placed closely on a circle, and antonyms such as happiness and sadness are placed at the opposite positions on the circle. Furthermore, each feeling is displayed by a direction and magnitude of a vector on two-dimensional coordinate axes. The difference in the vector direction between feelings represents each correlation coefficient. Specifically, an unpleasant (negative) feeling is assumed to be, for example, anger, frustration, boredom, and depression. A pleasant (positive) feeling is assumed to be, for example, happiness, joy, delight, and satisfaction.

A specific estimation algorithm for a feeling is not particularly limited, and various feeling estimation algorithms can be applied. Furthermore, a simple algorithm may be used. For example, estimation may be performed on the basis of a predetermined condition (threshold value) that a combination of a heart rate average of 80/min or more and a smile index of 70 or more is regarded as representing "delightful feeling". The subject-specific feeling estimation unit 214 can estimate a feeling of the image capturing person on the basis of the sensor data in a time zone (fixed time zone) in which the image capturing person has kept gazing at the subject. Specifically, for example, the subject-specific feeling estimation unit 214 may calculate a positive feeling index in one example of feelings on the basis of an analysis result (e.g., pulse average and smile index) of sensor data of the image capturing person for each subject. Furthermore, the subject-specific feeling estimation unit 214 may further calculate a negative feeling index, or calculate another feeling index. Furthermore, the subject-specific feeling estimation unit 214 may calculate a feeling index (interest index and attention feeling index) in further consideration of a degree of attention for each subject (e.g., calculate a high positive feeling index in a case where attention is paid with a smile, calculate a low positive feeling index in a case where attention is paid with an expression of disgust, and the like). Which sensor data is used, what feeling is estimated, whether or not a line-of-sight (degree of attention) is considered, and the like, may be set at the side of a system in advance, or selected by a user (image capturing person or viewer of the captured image).

The subject-specific feeling estimation unit 214 calculates the positive feeling index for each subject as follows, for example.

Subject ID1: Positive feeling Index of 20
Subject ID2: Positive feeling Index of 95
Subject ID3: Positive feeling Index of 0
Subject ID4: Positive feeling Index of 0
Subject ID5: Positive feeling Index of −50

The image processing unit 215 treats each subject appearing in the captured image on the basis of feeling information (feeling index) for each subject calculated by the subject-specific feeling estimation unit 214. Alternatively, the image processing unit 215 may treat each subject appearing in the captured image on the basis of a degree of attention for each subject calculated by the degree-of-attention calculation unit 212.

Examples of image treatment include, for example, treatment of pixels of a subject itself (e.g., blurring, scaling, deletion, and color change). For example, the image processing unit 215 enlarges a subject of interest in accordance with the height of the positive feeling index. In a case where the positive feeling index is lower than a predetermined value (or in a case where a degree of attention is lower than a predetermined value), the image processing unit 215 deletes the subject. The image processing unit 215 blurs the subject in according with a low positive feeling index. Furthermore, for example, the image processing unit 215 may perform treatment of highlighting the color of a subject having the highest positive feeling index (or subject having the highest degree of attention) (e.g., only a corresponding subject is expressed in color, and all of other regions are converted into black and white or sepia, and the like).

Furthermore, in another example of image treatment, a method of displaying feeling information with a character and a symbol (e.g., displaying characters such as "delightful", "sad", "impressed", "happy", "looking", and "not looking" near the subject) and a method of visualizing feeling information for each subject near the subject in an expression other than a character, such as a graph, a figure, and an icon, are conceivable, for example.

The image processing unit 215 may perform at least one of these method, or may perform these method in either combination.

Note that what kind of image treatment method is used may be set on the side of a system in advance, or may be selected by a user (image capturing person or a viewer of the captured image). For example, the user can specify that an image is treated by using a specific feeling (e.g., only "delight", only "interest", or the like) among analyzed feelings.

Furthermore, the image processing unit 215 may perform machine learning on the basis of, for example, a user selection history, and select an optimum approach of image treatment (e.g., approach of image treatment preferred by the user).

Furthermore, the image processing unit 215 may treat a plurality of images, and output the treated image. In this case, the user can bookmark a favorite among the plurality of treated images, and save the favorite in his/her terminal.

Furthermore, at the time of outputting the treated captured image to the display 30, the image processing unit 215 may together present information regarding the treatment such as on the basis of what kind of feeling the treatment has been performed, on the basis of what kind of sensor data the feeling has been estimated, and what kind of image treatment method has been used. As a result, in a case where the user is an image capturing person, the user can grasp, for example, emotion (e.g., which subject the user has paid attention to and to which subject the user has had a positive feeling) to each subject at the time of his/her capturing. Furthermore, in a case where the user is not the image capturing person, the user can understand, for example, emotion to each subject at the time of capturing performed by the image capturing person. Furthermore, in a case where particularly a plurality of treated images is output, on the basis of what kind of information each treated image has been treated is indicated to the user. If the user is the image capturing person, the user can select a captured image closer to the impression at the time of his/her capturing.

(Communication Unit 22)

The communication unit 22 is connected to an external apparatus in a wired or wireless manner, and transmits/receives data to/from the external apparatus. The communication unit 22 is communicably connected to the external apparatus by, for example, a wired/wireless local area network (LAN), Wi-Fi (registered trademark), Bluetooth (registered trademark), infrared communication, short-range communication, a portable communication network (long term evolution (LTE) and a third generation mobile communication system (3G)) and the like.

For example, the communication unit 22 receives a captured image, data regarding a line-of-sight of the image capturing person for each subject, and sensor data of the image capturing person for each subject from the input apparatus 10. Furthermore, the communication unit 22 transmits an image generated by the image processing unit 215 or information for displaying the image to the display 30 (one example of the external apparatus). In the image, a subject is treated on the basis of information regarding feelings of the image capturing person for each subject.

(Storage Unit 23)

The storage unit 23 is implemented by a read only memory (ROM) and a random access memory (RAM). For example, a program and an arithmetic parameter to be used for processing at the control unit 21 are stored in the ROM. The RAM temporarily stores, for example, a parameter that appropriately changes. For example, a feeling estimation algorithm, a program for an image treatment algorithm, and an arithmetic parameter are stored.

Furthermore, the storage unit 23 stores a captured image, subject-specific data regarding a line-of-sight, and subject-specific sensor data in association with each other. Furthermore, the storage unit 23 may further store a subject-specific degree of attention and subject-specific feeling information. Furthermore, the storage unit 23 may further store an image treated on the basis of the subject-specific degree of attention and the feeling information.

The configuration of the processor 20 according to the embodiment has been specifically described above. Note that the configuration of the processor 20 illustrated in FIG. 5 is one example, and the embodiment is not limited thereto. For example, at least a part of the configuration of the processor 20 may be in an external apparatus, or at least a part of each function of the control unit 21 may be in the external apparatus.

Furthermore, for example, in a case where the processor 20 is implemented by a server on a network, at least a part of the configuration of the processor 20 can be implemented by the input apparatus 10, the display 30, or an information processing apparatus (e.g., a so-called edge server and the like) having a communication distance relatively close to the input apparatus 10 or the display 30. As described above, appropriately distributing the configurations of the processor 20 enables improvement of real-time performance, reduction of a processing load, and ensured security.

Furthermore, all of each configuration of the control unit 21 and the storage unit 23 illustrated in FIG. 5 may be provided in the camera 11 or the display 30 (or single apparatus in which the camera 11 and the display 30 are integrated). The information processing system according to the embodiment may be operated by an application of the camera 11 or the display 30 (or single apparatus in which the camera 11 and the display 30 are integrated).

3. Operation Processing

Then, operation processing of an information processing system according to the embodiment will be specifically described with reference to FIG. 7.

Figure 7:
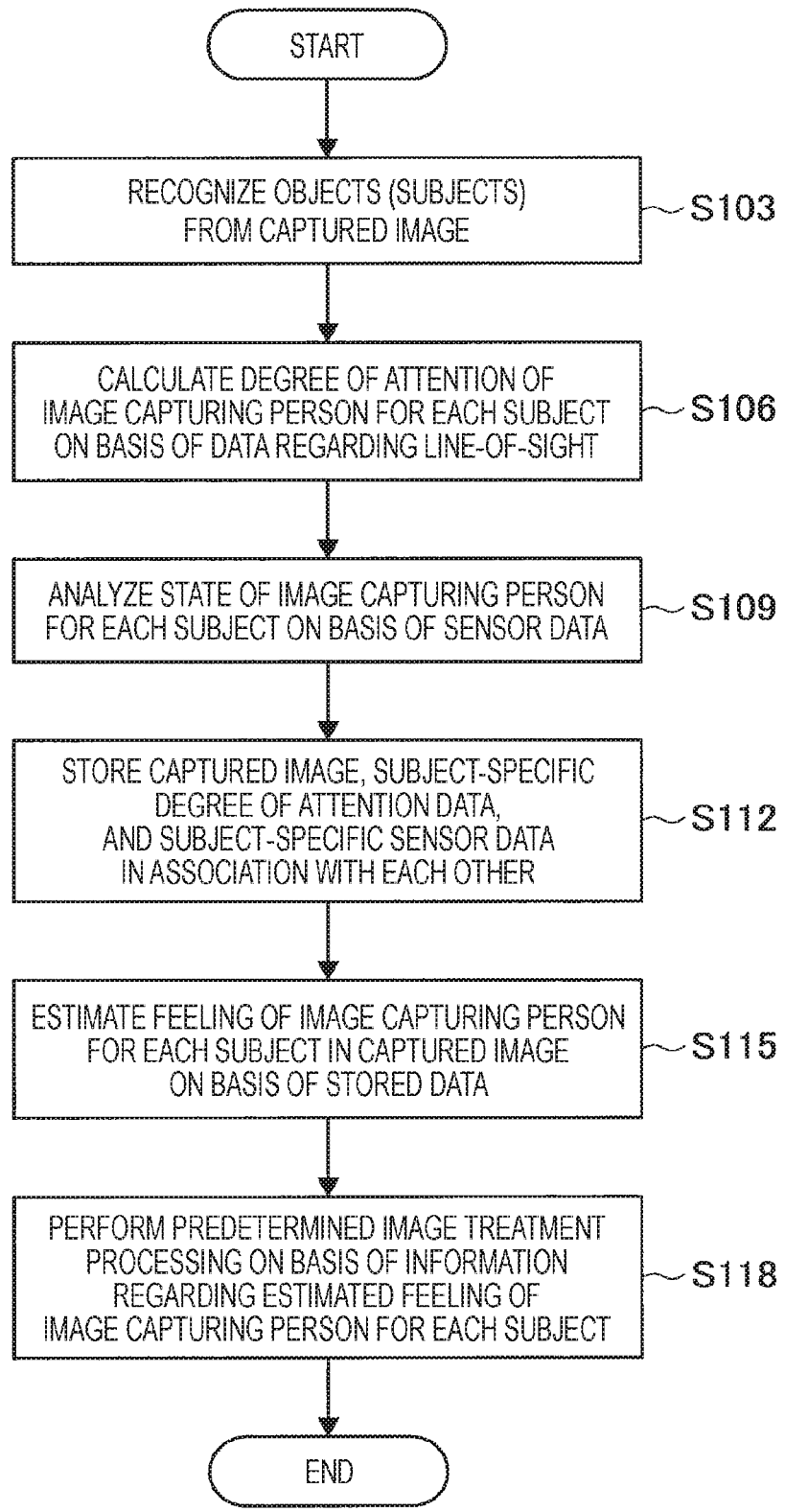
FIG. 7 is a flowchart illustrating one example of image processing according to the embodiment.

FIG. 7 is a flowchart illustrating one example of image processing according to the embodiment. As illustrated in FIG. 7, first, the object recognition unit 211 of the processor 20 recognizes one or more objects (subjects) from a captured image (Step S103).

Next, the degree-of-attention calculation unit 212 calculates a degree of attention of an image capturing person for each subject on the basis of data, corresponding to the captured image, regarding a line-of-sight of the image capturing person at the time of capturing (Step S106).

Next, the subject-specific feeling estimation unit 214 analyzes a state of the image capturing person for each subject on the basis of sensor data, corresponding to the captured image, of the image capturing person at the time of capturing (Step S109).

Next, the control unit 21 associates the calculated subject-specific degree of attention data and the analyzed subject-specific sensor data with the captured image, and stores the image in the storage unit 23 (Step S112).

Then, the subject-specific feeling estimation unit 214 estimates a feeling of the image capturing person for each subject in the captured image on the basis of stored data (subject-specific degree of attention data or subject-specific sensor data) (Step S115).

Then, the image processing unit 215 performs predetermined image treatment processing on the captured image on the basis of the information regarding estimated feeling of the image capturing person for each subject (Step S115). Note that the image processing unit 215 may perform predetermined image treatment processing on the captured image on the basis of the estimated degree of attention of the image capturing person for each subject.

One example of the operation processing according to the embodiment has been described above. Note that the operation processing illustrated in FIG. 7 is one example, and the disclosure is not limited to the example illustrated in FIG. 7. For example, the disclosure is not limited to the order of the steps illustrated in FIG. 7. At least one of the steps may be processed in parallel, or may be processed in the reverse order. For example, the processing of Step S106 and that of Step S109 may be performed in parallel, or may be performed in the reverse order.

Furthermore, not all pieces of processing illustrated in FIG. 7 need be performed. For example, the storage processing illustrated in Step S112 may be skipped.

Furthermore, not all pieces of processing illustrated in FIG. 7 need be performed in a single apparatus. For example, a plurality of apparatuses may perform the pieces of processing. For example, the input apparatus 10 may perform the processing of Steps S103 to S106. The processor 20 may perform the processing of Steps S109 to S115. The display 30 may perform the processing of Step S118.

Furthermore, each processing illustrated in FIG. 7 does not necessarily need to be performed sequentially in terms of time. For example, the processing illustrated in steps S103 to S112 may be performed immediately each time a new captured image is acquired or at the time when the certain number of captured images are accumulated. Then, the processing illustrated in Steps S115 to S118 may be performed at predetermined timing (e.g., at the time of receiving a user request, on a set cycle, or the like).

4. Example of Image Treatment

Figure 8:
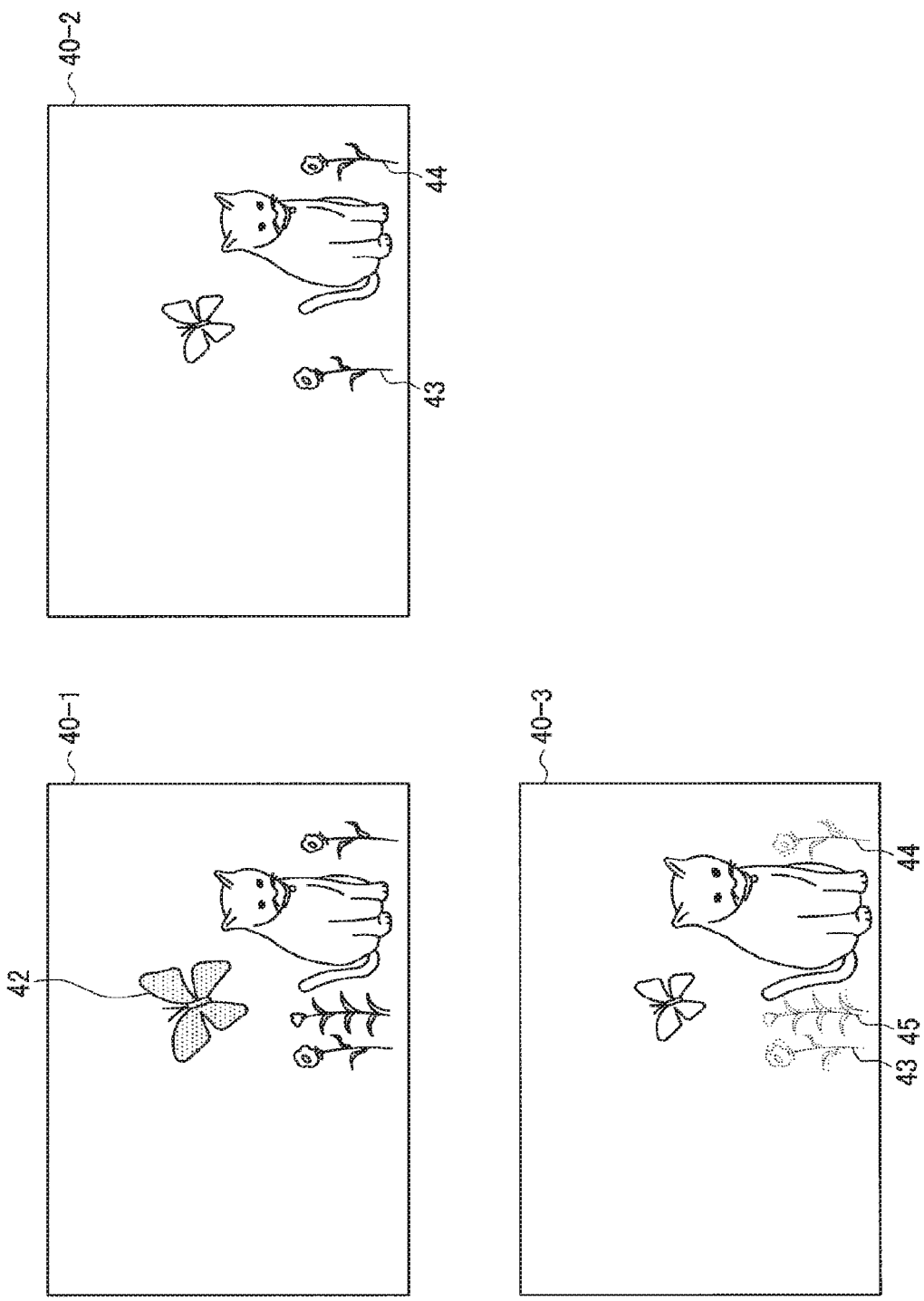
FIG. 8 illustrates one example of image treatment according to the embodiment according to the embodiment.

Next, a specific example of image treatment according to the embodiment will be described with reference to FIG. 8. FIG. 8 illustrates a specific example of a case where predetermined image treatment is performed on the captured image 40 illustrated in FIG. 6 on the basis of information regarding feelings of an imaging person or a degree of attention for each subject.

For example, in a case where the subject 42 (see FIG. 6) of a butterfly has the highest positive feeling index, treatment processing of enlarging the subject 42 and further highlighting the color of the subject 42 (e.g., sharpening a color, darkening, increasing saturation, lightening other parts, and desaturating other parts) as in a treated image 40-1 in FIG. 8 may be performed. As a result, a captured image closer to the reality that the image capturing person has felt larger presence of the butterfly at the time of looking with his/her naked eyes can be presented. The image capturing person can look without a feeling of difference from the time of looking with the naked eyes and capturing. Furthermore, a viewer can experience the realistic feeling of the time of capturing.

Furthermore, for example, in a case where the subject 45 (see FIG. 6) of the third flower has a positive feeling index of minus (or case where a degree of attention is zero (case where the third flower is not seen), for example), treatment processing of deleting the subject 45 may be performed as in a treated image 40-2 in FIG. 8. As a result, the flower, which gives almost no impression at the time of being seen by the image capturing person with his/her naked eyes, is deleted. The image capturing person can acquire a captured image (in which the flower does not disturb the scenery) that gives an impression at the time of looking with the naked eyes.

Furthermore, for example, in a case where the positive feeling indices of the subject 43 of the first flower, the subject 44 of the second flower, and the subject 45 of the third flower (see FIG. 6) are lower than a predetermined value, treatment processing of blurring the subject 43, the subject 44 and the subject 45 may be performed as in a treated image 40-3 in FIG. 8. As a result, the flowers, which do not leave much impression at the time of being seen by the image capturing person with the naked eyes, are blurred. The image capturing person can thereby acquire a captured image (in which the flowers do not disturb the scenery) that gives an impression of the time of looking with the naked eyes.

The above-described image treatment illustrated in FIG. 8 is one example, and the embodiment is not limited thereto. Furthermore, a plurality of pieces of treatment processing may be performed on a single captured image. For example, pieces of treatment processing, such as enlarging, blurring, and deleting a subject may be appropriately combined.

5. Hardware Configuration

The embodiment of the disclosure has been described above. The above-described processing of the processor 20 is achieved by cooperation of software and hardware of the later-described information processing apparatus.

Figure 9:
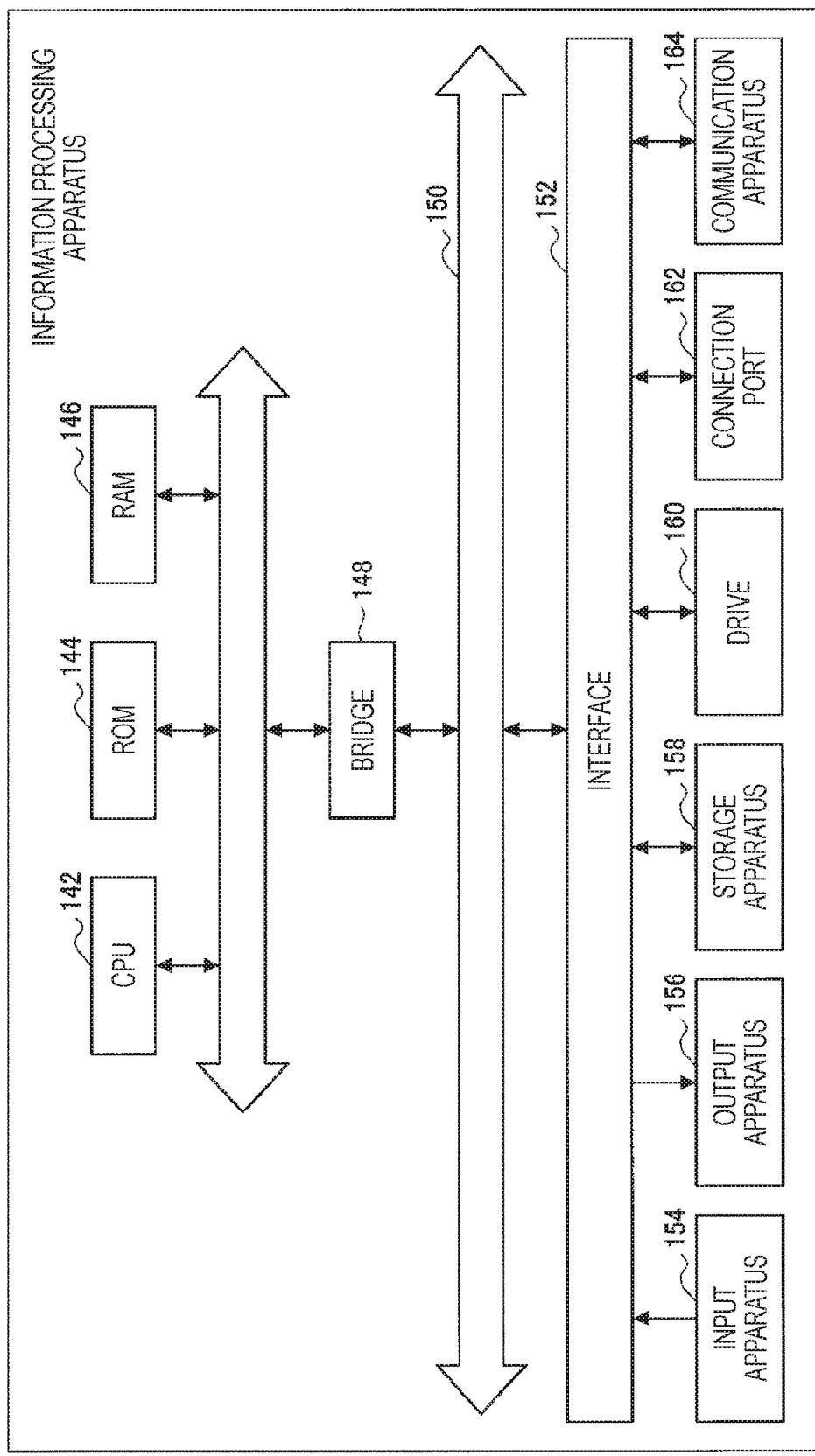
FIG. 9 is an explanatory diagram illustrating the hardware configuration of an information processing apparatus that implements the processor according to the disclosure.

FIG. 9 is an explanatory diagram illustrating the hardware configuration of an information processing apparatus that implements the processor 20 according to the disclosure. As illustrated in FIG. 9, the information processing apparatus includes a central processing unit (CPU) 142, a read only memory (ROM) 144, a random access memory (RAM) 146, a bridge 148, a bus 150, an interface 152, an input apparatus 154, an output apparatus 156, a storage apparatus 158, a drive 160, a connection port 162, and a communication apparatus 164.

The CPU 142 functions as an arithmetic processor and a controller. The CPU 142 implements operations of the object recognition unit 211, the degree-of-attention calculation unit 212, the sensor data analysis unit 213, the subject-specific feeling estimation unit 214, and the image processing unit 215 in the information processing apparatus (processor 20) in cooperation with various programs. Furthermore, the CPU 142 may be a microprocessor. For example, programs and arithmetic parameters used by the CPU 142 are stored in the ROM 144. The RAM 146 temporarily stores, for example, programs used in execution of the CPU 142 or parameters that appropriately change in the execution. The ROM 144 and the RAM 146 implement a part of the storage unit 23 in the information processing apparatus (processor 20). The CPU 142, the ROM 144, and the RAM 146 are connected to each other by an internal bus including, for example, a CPU bus.

The input apparatus 154 is an apparatus operated by a user, such as a mouse, a keyboard, a touch panel, a button, a microphone, a switch, and a lever, for example. The input apparatus 154 includes an input control circuit that generates an input signal on the basis of information input by the user and that outputs the input signal to the CPU 142. The user inputs various pieces of data to the information processing apparatus (processor 20) and instructs the information processing apparatus (processor 20) to perform processing operation by operating the input apparatus 154.

The output apparatus 156 includes an apparatus capable of notifying the user of the acquired information with senses of, for example, vision, hearing, and touch. The output apparatus 156 can be, for example, a display such as a liquid crystal display (LCD) apparatus and an organic electro-luminescence (EL) display, a voice output apparatus such as a speaker and headphones, vibrator, and the like. The output apparatus 156 outputs the result obtained by processing of the information processing apparatus as, for example, video such as text and an image, voice such as voice and audio, or vibration.

The storage apparatus 158 stores data. The storage apparatus 158 is configured as one example of the storage unit 23 of the information processing apparatus (processor 20). The storage apparatus 158 includes, for example, a magnetic storage unit device such as a hard disk drive (HDD), a semiconductor storage device, an optical storage device, a magneto-optical storage device, or the like. The storage apparatus 158 stores, for example, programs executed by the CPU 142, various pieces of data, various pieces of data acquired from the outside, and the like.

The drive 160 is a reader/writer for a storage medium, and is incorporated in or externally mounted on the information processing apparatus. The drive 160 reads information recorded in the attached removable storage medium, and outputs the information to the RAM 144. The removable recording medium includes, for example, a magnetic disk, an optical disk, a magneto-optical disk, and a semiconductor memory. Furthermore, the drive 160 can also write information on the removable storage medium.

The connection port 162 connects, for example, an external information processing apparatus or a peripheral instrument to the information processing apparatus. Furthermore, the connection port 162 may be, for example, a universal serial bus (USB) port, an IEEE 1394 port, a small computer system interface (SCSI) port, and the like. Furthermore, the connection port 162 may be, for example, an RS-232C port, an optical audio terminal, and a high-definition multimedia interface (HDMI) (registered trademark) port. Various pieces of data can be exchanged between the information processing apparatus and an external connection instrument by connecting the external connection instrument to the connection port 162. Furthermore, the connection port 162 may be, for example, a serial I/F for sensors, such as a universal asynchronous receiver transmitter (UART), an inter-integrated circuit (I2C), and a serial peripheral interface (SPI), a mobile industry processor interface (MIPI), a peripheral component interconnect (PCI)/PCI Express (I/F such as image data), and the like.

The communication apparatus 164 is one example of the communication unit 22 of the information processing apparatus (processor 20). The communication apparatus 164 is, for example, a communication interface including a communication device for connection to a network. Furthermore, the communication apparatus 164 may be an infrared communication compatible apparatus, a wireless local area network (LAN) compatible communication apparatus, a long term evolution (LTE) compatible communication apparatus, a Bluetooth (registered trademark) communication compatible apparatus, a Wi-Fi (registered trademark) communication compatible apparatus, and a wire communication apparatus that performs communication in a wired manner.

One example of the hardware configuration of the information processing apparatus (processor 20) has been illustrated above. Each of the above-described components may include a general-purpose member or hardware specialized in the function of each component. Such configuration can be appropriately changed in accordance with the technical levels at the time of implementation.

6. Conclusion

As described above, in the information processing system according to the embodiment of the disclosure, a feeling of an image capturing person for each subject of a captured image can be reflected in the captured image, and the realistic feeling of a scene felt by the image capturing person can be reproduced.

A preferred embodiment of the disclosure has been described in detail above with reference to the accompanying drawings, but the present technology is not limited to such an example. It is obvious that a person having ordinary skill in the art of the disclosure can arrive at various alternations or modifications within the scope of the technical ideas set forth in the claims. These alternations or modifications are understood to naturally fall within the technical scope of the disclosure.

For example, a computer program for causing hardware such as the above-described input apparatus 10, processor 20, and CPU, ROM, and RAM incorporated in the display 30 to perform functions of the input apparatus 10, the processor 20, or the display 30 can be created. Furthermore, a computer-readable storage medium storing the computer program is also provided.

Furthermore, a feeling of an image capturing person for each subject is reflected in the embodiment. The "subject" here is basically an "object" extracted from a captured image by object recognition as described above. The disclosure, however, is not limited thereto, and the "subject" is only required to be a region (pixel), divided by a boundary, of the captured image in the specification. For example, in a case where an imaging person remembers that there was a bench here in the past, gazes at one point on a road, and captures an image of a place of memories with a feeling of nostalgia, the object recognition unit 211 may recognize a region (part of the road), which the image capturing person has gazed at, as a "subject" on the basis of data regarding a detected line-of-sight of the image capturing person. In this case, the image processing unit 215 can reflect emotion of the image capturing person, and reproduce a scene closer to impression as seen by the image capturing person with his/her naked eyes by, for example, performing treatment of highlighting (increasing the presence of) such a "part of the road".

Furthermore, the effects described herein are merely illustrative or exemplary, and not limitative. That is, the technique according to the disclosure may have other effects that are obvious to a skilled person from the description of the present specification, together with or in place of the above-described effects.

Note that the present technology can also have the configuration as follows.

(1)
An information processing apparatus including:
a recognition unit that recognizes one or more subjects from a captured image;
an estimation unit that estimates a feeling of an image capturing person for each of the recognized subjects on the basis of data regarding a line-of-sight of the image capturing person and sensor data of the image capturing person associated with the captured image; and
an image processing unit that performs image processing of reflecting the feeling for each of the subjects in the captured image.

(2)
The information processing apparatus according to (1), in which the data regarding a line-of-sight and the sensor data are time-series data from a predetermined period of time before acquisition of the captured image to the acquisition.

(3)
The information processing apparatus according to (2),
in which the estimation unit estimates a feeling of the image capturing person in a time zone in which the image capturing person has kept gazing at the subject, the time zone being determined on the basis of the data regarding a line-of-sight.

(4)
The information processing apparatus according to (3),
in which the estimation unit estimates a feeling of the image capturing person on the basis of the sensor data.

(5)
The information processing apparatus according to (3) or (4),
in which the estimation unit estimates a feeling of the image capturing person on the basis of a degree of attention of the image capturing person to the subject, the degree of attention being calculated from the data regarding a line-of-sight.

(6)
The information processing apparatus according to any one of (2) to (5),
in which the sensor data includes at least one of biosensor data, voice data, imaging data, motion sensor data, or data calculated from one or more pieces of sensor data.

(7)
The information processing apparatus according to any one of (2) to (6),
in which the image processing unit treats a subject or a region other than the subject in accordance with a feeling of the image capturing person to the subject.

(8)
The information processing apparatus according to (7),
in which the image processing unit changes a pixel in a subject or a region other than the subject in accordance with a positive feeling of the image capturing person to the subject.

(9)

The information processing apparatus according to any one of (2) to (8), in which the image processing unit performs treatment of adding display indicating a feeling of the image capturing person to a subject in the captured image.

(10)

The information processing apparatus according to (9), in which the display indicating a feeling of the image capturing person includes at least one of a character, a symbol, a graph, a figure, or an icon.

(11)

The information processing apparatus according to any one of (2) to (10), in which the image processing unit generates a plurality of treated images by using at least different kinds of feelings, a feeling estimated by using different pieces of sensor data, or different treatment methods.

(12)

The information processing apparatus according to any one of (2) to (11), further including a transmission unit that transmits a treated image generated by the image processing unit to an external apparatus.

(13)

The information processing apparatus according to any one of (2) to (12), further including a display unit that displays a treated image generated by the image processing unit.

(14)

The information processing apparatus according to (12) or (13), in which the information processing apparatus outputs information regarding a kind of feeling that has been used in image treatment, sensor data that has been used in estimation of a feeling, or a treatment method that has been used in image treatment together with the treated image.

(15)

An information processing method including:

recognizing, by a processor, one or more subjects from a captured image;

estimating, by the processor, a feeling of an image capturing person for each of the recognized subjects on the basis of data regarding a line-of-sight of the image capturing person and sensor data of the image capturing person associated with the captured image; and performing, by the processor, image processing of reflecting the feeling for each of the subjects in the captured image.

(16)

A program causing a computer to function as:

a recognition unit that recognizes one or more subjects from a captured image;

an estimation unit that estimates a feeling of an image capturing person for each of the recognized subjects on the basis of data regarding a line-of-sight of the image capturing person and sensor data of the image capturing person associated with the captured image; and an image processing unit that performs image processing of reflecting the feeling for each of the subjects in the captured image.

REFERENCE SIGNS LIST 1, 1a, 1b Information processing system
10 Input apparatus
10b Glass apparatus
11 Camera
11a Camera apparatus
11b Capturing camera
12 Line-of-sight detection sensor
12b Camera
13 Sensor device
13a Biosensor
20 Processor
20a Image processor
20b Server
21 Control unit
211 Object recognition unit
212 Degree-of-attention calculation unit
213 Sensor data analysis unit
214 Subject-specific feeling estimation unit
215 Image processing unit
22 Communication unit
23 Storage unit
30 Display
30a Display unit
30b Information processing terminal

The invention claimed is:

1. An information processing apparatus, comprising:
a recognition unit configured to recognize a plurality of subjects from a captured image;
an estimation unit configured to estimate a feeling of an image capturing person for each subject of the recognized plurality of subjects based on data regarding a line-of-sight of the image capturing person and sensor data of the image capturing person associated with the captured image; and
an image processing unit configured to:
execute an image process on the captured image for indicating the estimated feeling for each subject of the plurality of subjects in the captured image; and
change a pixel corresponding to at least one subject of the plurality of subjects in the captured image based on the execution of the image process and the estimated feeling.

2. The information processing apparatus according to claim 1, wherein the data regarding the line-of-sight and the sensor data are time-series data from a determined period of time before acquisition of the captured image to the acquisition of the captured image.

3. The information processing apparatus according to claim 2, wherein
the estimation unit is further configured to estimate the feeling of the image capturing person in a time zone in which the image capturing person has gazed at the at least one subject, and
the time zone is based on a basis of the data regarding the line-of-sight.

4. The information processing apparatus according to claim 3, wherein the estimation unit is further configured to estimate the feeling of the image capturing person based on the sensor data.

5. The information processing apparatus according to claim 3, further comprising a degree-of-attention calculation unit configured to calculate a degree of attention of the image capturing person to each subject of the plurality of subjects, wherein
the estimation unit is further configured to estimate the feeling of the image capturing person based on the degree of attention of the image capturing person, and
the degree of attention is calculated from the data regarding the line-of-sight.

6. The information processing apparatus according to claim 2, wherein the sensor data includes at least one of biosensor data, voice data, imaging data, motion sensor data, or data calculated from at least one piece of the sensor data.

7. The information processing apparatus according to claim 2, wherein the image processing unit is further configured to treat one of the at least one subject or a region of the captured image other than the at least one subject based on the feeling of the image capturing person to the at least one subject.

8. The information processing apparatus according to claim 7, wherein the image processing unit is further configured to change a pixel in the region of the captured image other than the at least one subject based on a positive feeling of the image capturing person to the at least one subject.

9. The information processing apparatus according to claim 2, wherein the image processing unit is further configured to execute a process of addition of display indicating the feeling of the image capturing person to the at least one subject in the captured image.

10. The information processing apparatus according to claim 9, wherein the display indicating the feeling of the image capturing person includes at least one of a character, a symbol, a graph, a figure, or an icon.

11. The information processing apparatus according to claim 2, wherein the image processing unit is further configured to generate a plurality of treated images based on at least one of different kinds of feelings, the feeling estimated by different pieces of the sensor data, or different treatment methods.

12. The information processing apparatus according to claim 2, further comprising a transmission unit configured to transmit a treated image to an external apparatus, wherein the treated image comprises the at least one subject.

13. The information processing apparatus according to claim 2, further comprising a display unit, wherein
the image processing unit is further configured to generate a treated image based on the execution of the image process, and
the display unit is further configured to display the treated image.

14. The information processing apparatus according to claim 12, wherein the information processing apparatus is further configured to output information related to a kind of feeling used in the image process, the sensor data used in estimation of the feeling, or a treatment method used in the image process together with the treated image.

15. An information processing method, comprising:
recognizing, by a processor, a plurality of subjects from a captured image;
estimating, by the processor, a feeling of an image capturing person for each subject of the recognized plurality of subjects based on data regarding a line-of-sight of the image capturing person and sensor data of the image capturing person associated with the captured image;
executing, by the processor, an image process on the captured image for indicating the estimated feeling for each subject of the plurality of subjects in the captured image; and
changing, by the processor, a pixel corresponding to at least one subject of the plurality of subjects in the captured image based on the execution of the image process and the estimated feeling.

16. A non-transitory computer-readable medium having stored thereon, computer executable-instructions that, when executed by a processor, cause the processor to execute operations, the operations comprising:
recognizing a plurality of subjects from a captured image;
estimating a feeling of an image capturing person for each subject of the recognized plurality of subjects based on data regarding a line-of-sight of the image capturing person and sensor data of the image capturing person associated with the captured image;
executing an image process on the captured image for indicating the estimated feeling for each subject of the plurality of subjects in the captured image; and
changing a pixel corresponding to at least one subject of the plurality of subjects in the captured image based on the execution of the image process and the estimated feeling.

17. An information processing apparatus, comprising:
a recognition unit configured to recognize one or more subjects from a captured image;
an estimation unit configured to estimate a feeling of an image capturing person for each subject of the one or more subjects based on data regarding a line-of-sight of the image capturing person and sensor data of the image capturing person associated with the captured image, wherein the data regarding the line-of-sight and the sensor data are time-series data from a determined period of time before acquisition of the captured image to the acquisition of the captured image; and
an image processing unit configured to:
execute an image process on the captured image for reflecting the feeling for each subject of the one or more subjects in the captured image;
treat one of a subject of the one or more subjects or a region of the captured image other than the subject based on the feeling of the image capturing person; and
change a pixel in one of the subject or the region other than the subject based on a positive feeling of the image capturing person to the subject.

* * * * *